US006931278B1

(12) United States Patent
Kroll et al.

(10) Patent No.: US 6,931,278 B1
(45) Date of Patent: Aug. 16, 2005

(54) IMPLANTABLE CARDIOVERTER DEFIBRILLATOR HAVING FAST ACTION OPERATION

(75) Inventors: Mark W. Kroll, Simi Valley, CA (US); Gabriel A. Mouchawar, Valencia, CA (US); Timothy A. Fayram, Gilroy, CA (US)

(73) Assignee: Pacesetter, Inc., Sylmar, CA (US)

( * ) Notice: Subject to any disclaimer, the term of this patent is extended or adjusted under 35 U.S.C. 154(b) by 331 days.

(21) Appl. No.: 10/313,223

(22) Filed: Dec. 6, 2002

(51) Int. Cl.[7] ............................................. A61N 1/39
(52) U.S. Cl. ........................................................ 607/5
(58) Field of Search ........................................ 607/4–8

(56) References Cited

U.S. PATENT DOCUMENTS

| | | | | |
|---|---|---|---|---|
| 4,953,551 | A | | 9/1990 | Mehra et al. ............. 128/419 D |
| 5,314,448 | A | * | 5/1994 | Kroll et al. ....................... 607/5 |
| 5,385,575 | A | * | 1/1995 | Adams ............................ 607/5 |
| 5,439,482 | A | | 8/1995 | Adams et al. ................... 607/5 |
| 5,679,953 | A | | 10/1997 | Ananth et al. ............ 250/338.1 |
| 5,827,326 | A | | 10/1998 | Kroll et al. ...................... 607/5 |
| 5,919,211 | A | | 7/1999 | Adams ............................ 607/5 |
| 5,957,956 | A | | 9/1999 | Kroll et al. ...................... 607/5 |
| 6,094,597 | A | | 7/2000 | Wold .............................. 607/5 |
| 6,275,729 | B1 | | 8/2001 | O'Phelan et al. ............... 607/5 |
| 2001/0016757 | A1 | | 8/2001 | O'Phelan et al. ............... 607/5 |
| 2002/0035380 | A1 | | 3/2002 | Rissmann et al. .............. 607/4 |

FOREIGN PATENT DOCUMENTS

| | | | | |
|---|---|---|---|---|
| EP | 0642 362 | | 6/1998 | ............ A61N 1/39 |
| WO | WO 94/00193 | | 1/1994 | ............ A61N 1/39 |
| WO | WO 96/22811 | | 8/1996 | ............ A61N 1/39 |

* cited by examiner

*Primary Examiner*—Scott M. Getzow

(57) ABSTRACT

An implantable cardiac rhythm management device has a housing containing rhythm management circuitry. The circuitry includes a battery, a transformer, and a capacitor connected via charging circuitry that operates to transmit current from the battery to charge the capacitor. A number of leads connected to the circuitry operate to transmit a shock from the capacitor to cardiac tissue outside of the housing. The capacitor has a smaller volume than the combined volume of the battery and transformer, such that it reaches a selected charge voltage within a limited time interval. The device may operate to limit capacitor charging to less than a selected energy storage capability at a given voltage, and components may be selected to limit charging time to less than 2 seconds. The component selection and charge duration may be based on a time-based function of defibrillation threshold (DFT).

20 Claims, 5 Drawing Sheets

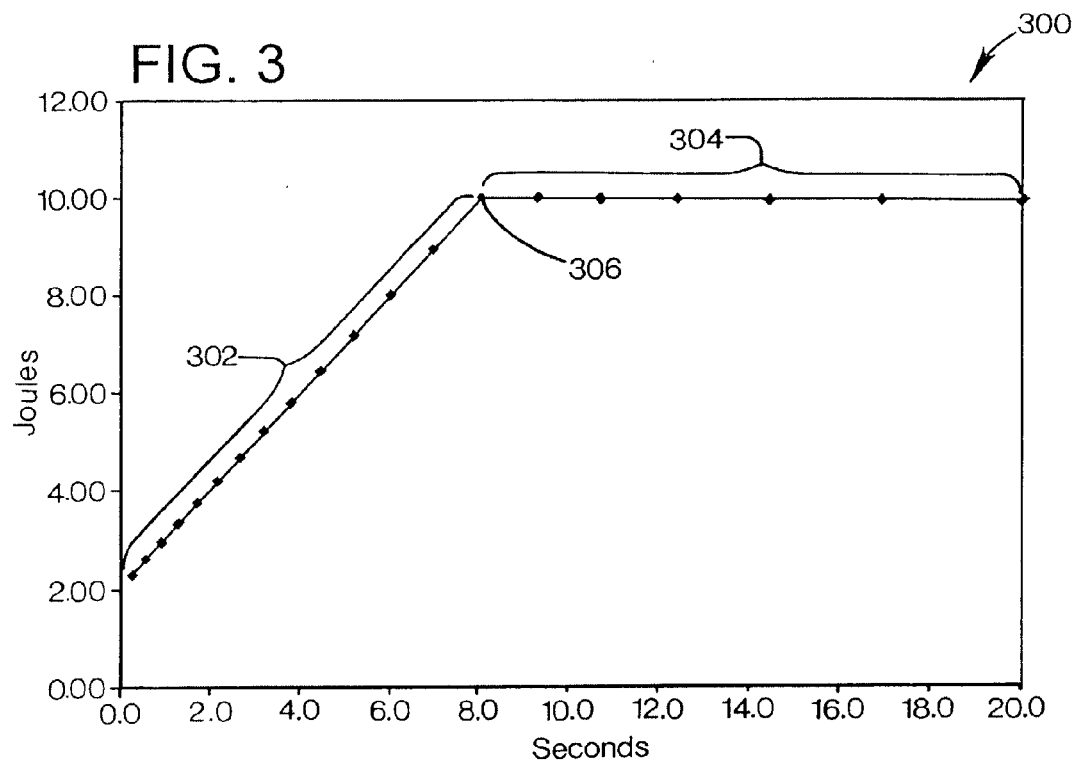
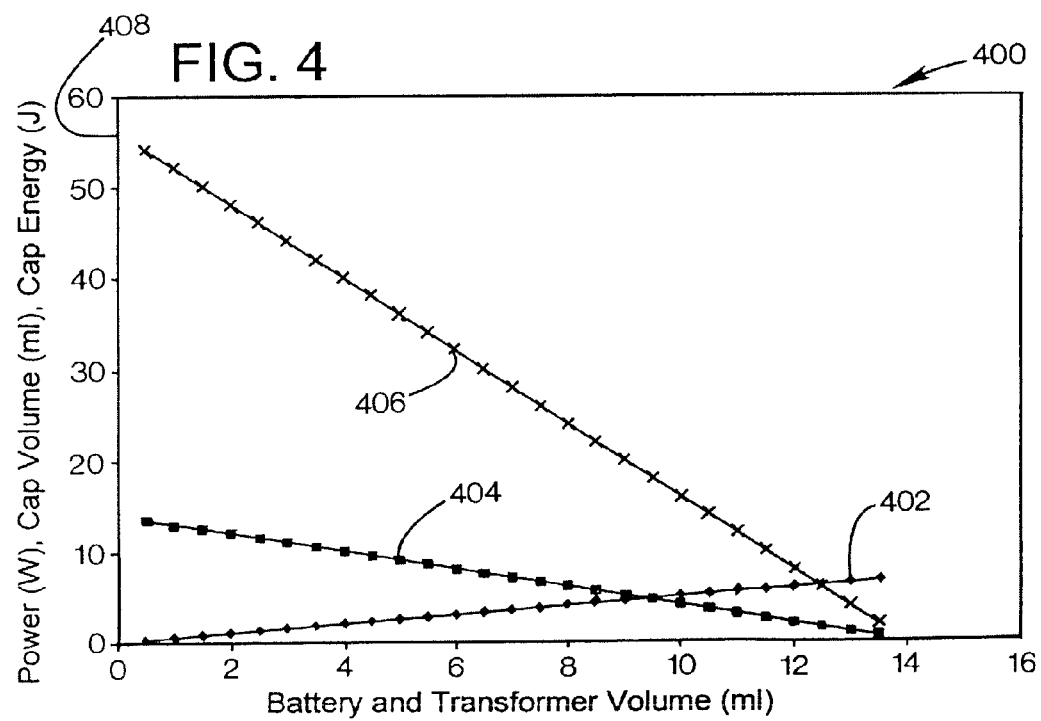

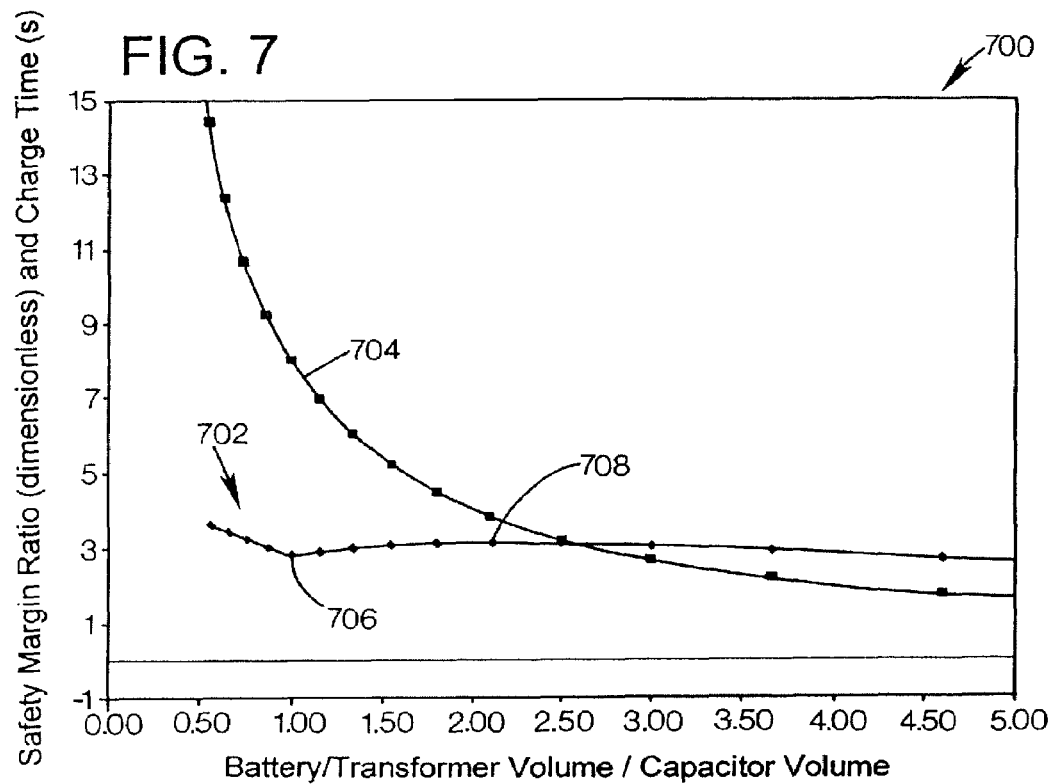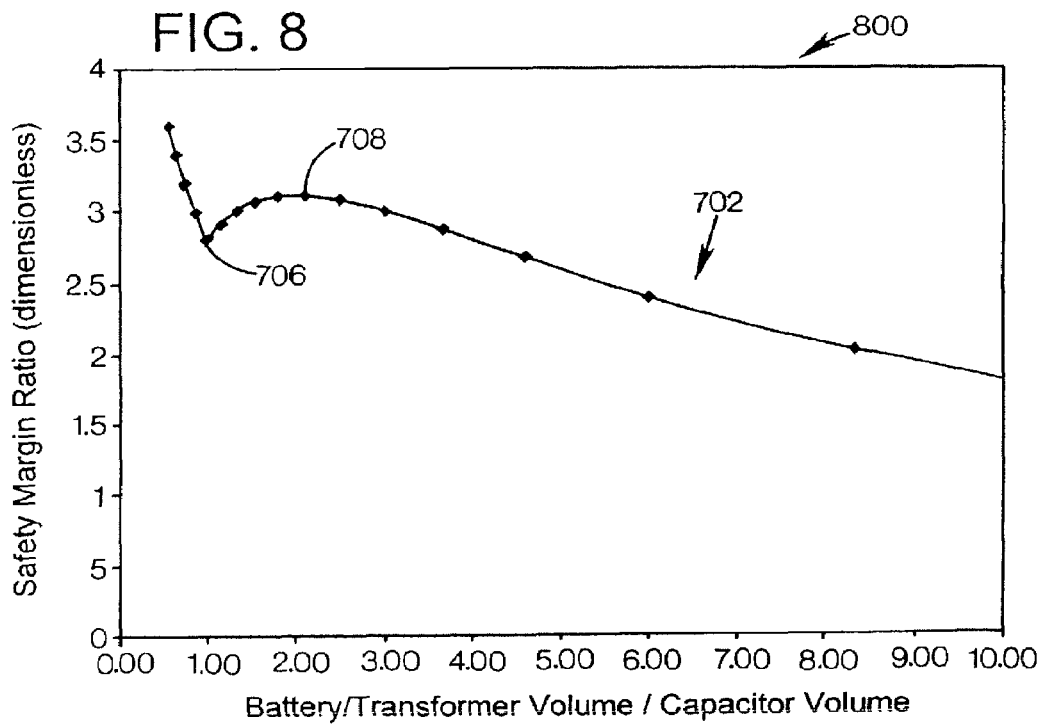

IMPLANTABLE CARDIOVERTER DEFIBRILLATOR HAVING FAST ACTION OPERATION

FIELD OF THE INVENTION

This invention relates to implantable medical devices, and more particularly to battery and capacitor configurations of implantable cardioverter/defibrillators.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by detecting a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart. The capacitance of the capacitor is established to deliver a shock with an energy of 30–40 joules. In conventional devices, smaller capacitors are inadequate to deliver sufficient charge to provide effective therapy.

The time between detection of a cardiac and the delivery of the shock is an important concern. It is believed that more prompt therapy provides more effective results. For instance, a patient who experiences tachyarrhythmia may lose consciousness before therapy is delivered. This can lead to injuries from falling, or vehicle accidents should the patient be driving. In addition, it is believed that a major cause of death among some implanted patients is the progression to electromechanical disassociation (EMD), in which therapy restores electrical activity without restoring hemodynamic function, so that the affected cardiac cells fail to regain their blood-pumping function.

To provide shorter charge times and thus faster therapy delivery, conventional technology has employed larger batteries that deliver current to the capacitor at a higher rate. This has the disadvantage of requiring a larger overall implant package, or at least limits the amount of miniaturization that would otherwise be desired for patient comfort. Another approach to reduce charge time intervals has been to employ more sophisticated battery technology that provides higher current rates for a given size. However, this suffers from higher cost, and also limited miniaturization. Alternative approaches have employed networks of batteries having different characteristics that allow more rapid charging while not significantly limiting battery life. However, these approaches contribute to device complexity and cost.

Medical researchers (Gradaus, et al., PACE January 2002) have discovered that the defibrillation threshold (DFT) in humans is not constant, but is lower as the time interval to therapy is reduced. DFT is the amount of energy (typically measured in joules) required for effective therapy. The observed DFT reduction starts occurring only below very brief time intervals (less than about 8 seconds.) Thus, existing technology lacks the capability to charge capacitors in such a brief interval without accruing some of the disadvantages noted above regarding large and or expensive batteries. Therefore, there remains a need for a fact acting charging system that does not sacrifice size, cost, or complexity.

SUMMARY OF THE INVENTION

The disclosed embodiment overcomes the limitations of the prior art by providing an implantable cardiac rhythm management device. The device has a housing containing rhythm management circuitry. The circuitry includes a battery, a transformer, and a capacitor connected via charging circuitry that operates to transmit current from the battery to charge the capacitor. A number of leads connected to the circuitry operate to transmit a shock from the capacitor to cardiac tissue outside of the housing. The capacitor has a smaller volume than the combined volume of the battery and transformer, such that it reaches a selected charge voltage within a limited time interval. The device may operate to limit capacitor charging to less than a selected energy storage capability at a given voltage, and components may be selected to limit charging time to less than 2 seconds. The component selection and charge duration may be based on a time-based function of defibrillation threshold (DFT).

BRIEF DESCRIPTION OF THE DRAWINGS

Further features and advantages of the present invention may be more readily understood by reference to the following description taken in conjunction with the accompanying drawings, in which:

FIGS. 3–8 are charts illustrating the principles of operation of the preferred embodiment.

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
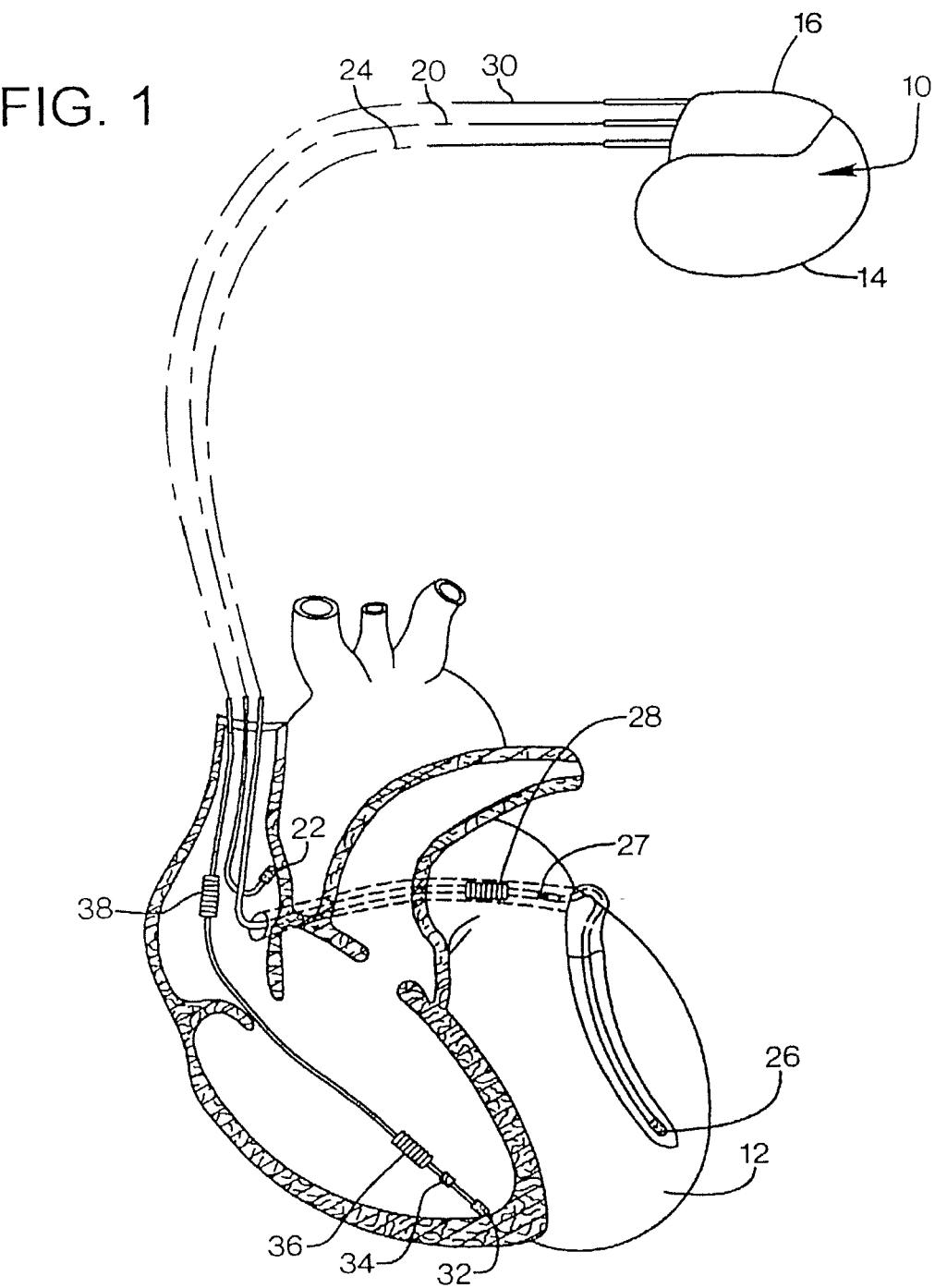
FIG. 1 is a simplified diagram illustrating an implantable stimulation device, having a prior art housing and header form, in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. The device 10 is shown in a form found in the prior art, while the rest of the elements and description are consistent with the preferred embodiment of the invention. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

The prior art form of the device 10 has a hollow, sealed metal housing 11 containing the circuitry discussed below, and a header 12 to which the leads are connected. The overall prior art device shape is a flat body with a rounded periphery. The header essentially forms one corner of the device, and protrudes from the housing. The header is attached to the housing at a pair of obtusely angled housing surfaces 13, 14, which form a shallow recess, and each of which faces away from the rest of the housing. The angle of the surfaces 13, 14 is about 120°.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a Superior Vena Cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
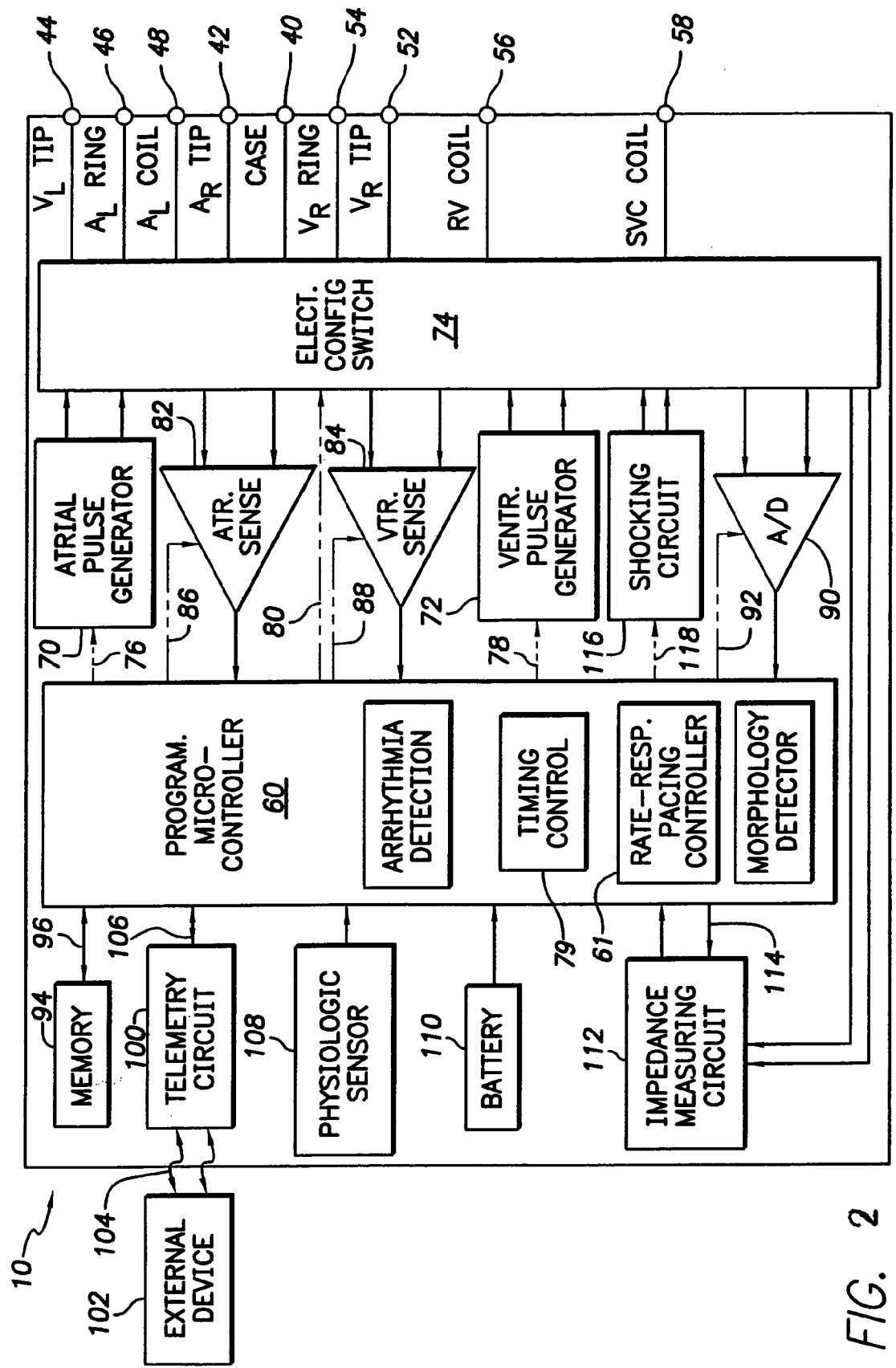
FIG. 2 is a functional block diagram of a multi-chamber implantable stimulation device according to the preferred embodiment illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10; which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, well in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In the preferred embodiment, the ratio of the capacitor volume to battery volume is substantially smaller than in conventional designs. This is a counterintuitive approach that is contrary to the conventional understanding of the needs of ICDs. In conventional ICDs, capacitor size is deliberately large, to provide an adequately large shock. The magnitude of the shock (conventionally 30–40 J) is established to provide a significant safety margin over the presumed defibrillation threshold (DFT). The safety margin ratio (SM) is the factor by which the shock exceeds the presumed DFT (e.g. a 30 J shock and a 10 J DFT) yields a safety margin of 3.) It is well-established that there are significant therapeutic advantages to employing a significant safety margin ratio in the range of 1.5 to 2.0, and that there are significant risks to operating too close to the DFT. Conventionally, any significant reduction in the capacitor size would be expected to reduce the safety factor unacceptably.

In the preferred embodiment, the capacitor size is reduced significantly, but the battery size is increased significantly. Not only does the increased battery size enable faster charging, but the reduced capacitor size further reduces the time to charge to a selected voltage (preferably 775V.) The charge level in the preferred embodiment is in the range of 10–15 J, which is about ½ to ⅓ of conventional designs. Because charge time is a function of the square of the charge (measured in coulombs, the reduction in charge amount has an even greater effect on shortening the charge time. This reduced charge level would be inadequate if the DFT were constant with respect to the time interval between a detected abnormality and delivery of the shock, and all conventional wisdom would strongly advise against trying to achieve the benefits of fast therapy when that therapy was well below the needed safety margin with respect to the DFT.

However, the preferred embodiment employs the discovery that DFT is not constant, by using a shock that is delivered much more quickly than was previously thought feasible to enjoy an ample margin of safety previously assumed unattainable for rapid charge times. The margin of safety is achieved with a low energy shock because of the newly-discovered fact that DFT is much lower when shocks are delivered quickly.

FIG. 3 is a graph 300 illustrating an exemplary defibrillation threshold (DFT) as a function of the time interval between detection and therapy, as published by Gradaus, noted above. The DFT is about 4 J at 2 seconds and increases to a maximum of 10 J at 8 seconds and beyond. The function in the 0–8 second range may be expressed as DFT=2+t, where t is the time interval in seconds. It is possible that further research will refine this function from its simplified form illustrated, and that there may not be a constant slope in the initial interval 302, nor perfect constancy of DFT in the subsequent period 304 after the transition point 306. However, the principle that DFT is significantly lower at the outset is the critical concept employed by the preferred embodiment, even if further research should show some deviation from the illustrated function. This may also include deviations among different patients.

FIG. 4 is a graph 400 illustrating the effect of varying the combined volume of the battery and transformer while holding the total volume of the high power components (battery, transformer, and capacitor) constant at 14 ml. This illustrates how the preferred embodiment parameters were arrived at. A line 402 indicates that the required charging power increases proportionately with the combined volume of the battery and transformer. The illustrated model uses a typical value of 0.5 net charging watts per ml of volume. A line 404 indicating the capacitor volume, which decreases as the battery (plus transformer) volume increases while the total volume is held constant. The capacitor energy is indicated by line 406 and is also calculated at 4 J/ml, based as a function of capacitor volume. The vertical axis 408 is labeled in units of watts (for charging power), milliliters (for capacitor volume), and joules (for capacitor energy, also referred to herein as capacitor size.) In conventional devices, high capacitor energies are employed (in the range of 30–40 J), representing values of battery volume toward the left of the graph.

Figure 5:
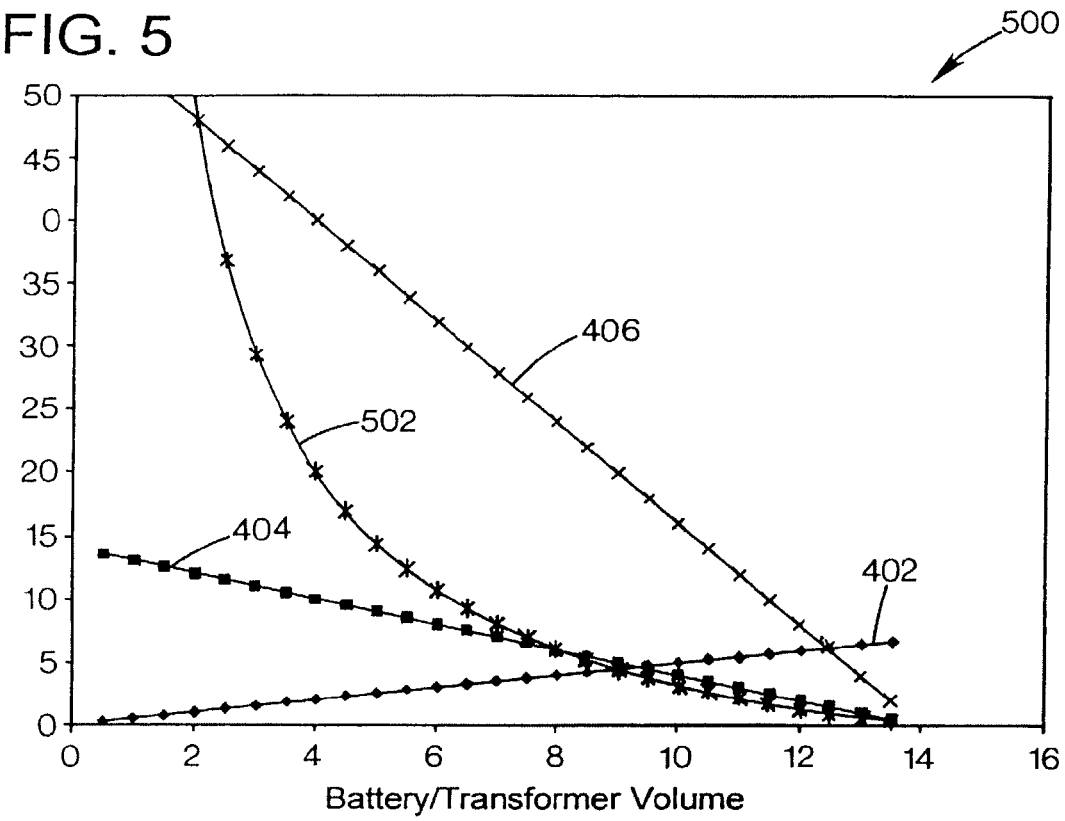

FIG. 5 is a graph 500 that includes the same lines 402, 404, and 406 as FIG. 4, with the same axis labels, plus the lower axis also serving as a time axis. A hyperbolic curve 502 indicates the charge time (in seconds) to maximum energy. That is, the time to fully charge the capacitor to the desired threshold voltage (e.g. 775 V). The charge time increases dramatically as volume of the battery plus transformer (BT) is decreased, both because of the reduced capability of the battery to charge, and because of the increased demand placed by a larger capacitor. This charge time function may be expressed as t=[4(14−BT)]/[BT].

Figure 6:
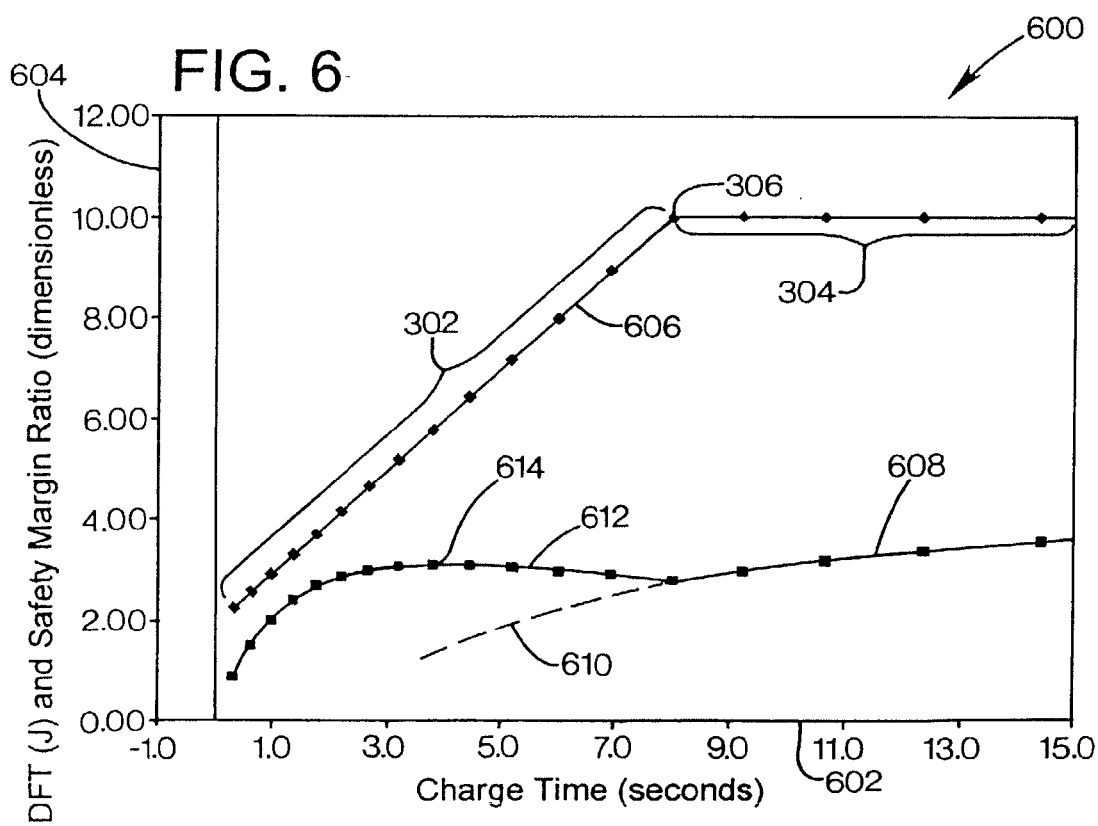

FIG. 6 is a graph 600 showing the unexpected indirect interaction between the charge time and the safety margin. The horizontal axis 602 is charge time in seconds, and the vertical axis indicates DFT in joules, and a dimensionless safety margin ratio. The DFT line 606 is illustrated as in FIG. 3. (The analysis ignores an unavoidable and slight additional delay of detection times, which does not effect the principle of the preferred embodiment.) Line 608 indicates a Safety Margin Ratio (SM), which is defined as the ratio of the energy available on the capacitor (at maximum charge) to the DFT at that time delay. In the range 304 at which DFT is essentially constant, the safety margin ratio increases at a diminishing rate over time. This can be expressed as the function: SM(t)=E/DFT=K*t/DFT, where "K" is a constant representing the charging speed of the battery and transformer system. Conventional devices operate in this range 304, with the charge time established to provide a duration long enough to reach an adequate safety margin ratio. However, the preferred embodiment operates in the faster range 302 in which it has long been believed that safety margins would be unavoidably inadequate. Essentially, prior devices avoided this range, and used advances (such as with battery and capacitor performance per unit volume) to raise the safety margin curve and thus allow progress leftward to faster times without sacrificing safety margin ratio. However, for a given state of technology, all efforts in the prior art have been made to avoid the assumed leftward extension 610 of the safety margin curve.

Because the DFT denominator of the safety margin ratio unexpectedly diminishes below point 306, the safety margin ratio unexpectedly rises as indicated by line segment 612. For instance, at the point at which the DFT is half its long term value, the safety margin ratio is double what would have been expected in line 610. The diminishment of the DFT in this range is significant enough to outweigh the diminishment of the conventionally-assumed safety margin, so that the safety margin rises to a local maximum 614 at about 3.5 seconds. The function that expresses this portion of the curve is SM=56/[(t+4)(t+2)]. At the local maximum 614, and in the range near it, the safety margin is at least 3. Because the curve is relatively flat in this range, a charge time of about 2 seconds yields a safety margin of about 3. While it is possible to gain a slightly higher safety margin ratio using prolonged charging times, it is believed that the increase in safety margin provides no significant benefit, while the delivery of more prompt therapy provides a significant added benefit. (For example, it permits the charging and delivery of a second shock if needed within a much shorter total interval.)

FIG. 7 is a graph 700 that illustrates how the SM ratio 702 and charge time 704 depend on the component volume ratio of the volume of the Battery plus transformer to that of the capacitor. To the left of the inflection point 706 is the curve segment on which conventional devices operate, with safety margin increasing for larger capacitors. This segment may be functionally expressed as approximately K1–K2* (component volume ratio) where K1 and K2 are constants determined by the DFT characteristics and the battery, transformer, and capacitor characteristics. The "component volume ratio" is the volume for the battery and transformer divided by the capacitor volume.

To the right of point 706 is the unexpected range at which the safety margin rises due to smaller capacitors being more rapidly charged, and larger batteries being capable of faster charging, allowing charge times short enough to reach the zone at which low DFT yields a high safety margin ratio. This segment may be functionally expressed as $K_1/[(K_2+R)(K_3+R]$, where R=BT volume/capacitor volume. In the battery and capacitor functional capabilities per unit volume discussed above for preferred embodiment technologies, a volume ratio of 1.0 happens to coincide with the point of inflection. Thus, the preferred embodiment employs a ratio greater than 1, so that the battery plus transformer have a greater volume than that of the capacitor. In the preferred embodiment, a local maximum SM 708 of about 3.0 is achieved at a volume ratio of about 2.0. Significant advantages are believed to achieved when the volume ratio is significantly above that corresponding to the point of inflection; volume ratios of 1.5 or greater provide the most significant benefits. A volume ratio of less than 2.5 is preferred with current components, to avoid a needlessly diminished safety margin ratio significantly below the peak illustrated in FIG. 7 and FIG. 8 as discussed below.

While similarly high or higher SM values may be achieved well to the left of the inflection point 706, this is only at the cost of extremely long charge times, with their attendant medical disadvantages. Of course, these charge times may be somewhat decreased, but only by increasing overall component volume (instead of constraining total component volume as in the illustration), or by employing more costly volume-efficient components.

FIG. 8 is a graph 800 essentially the same as FIG. 7, but with re-scaled axes to graphically emphasize the local maximum safety margin ratio shown in FIG. 7, demonstrating the advantage of having the battery (and transformer) about twice as big as the capacitor.

If a conventional ICD were used to attempt to exploit the Gradaus medical discoveries, they would be ineffective. For instance, if one employed a 15 s, 36 J device set to a first shock energy of 6 J, the device should charge within 2.5 seconds and defibrillate. The problem with this is that the safety margin ratio would be only 1.33, as calculated based on: DFT=4.5.J=2.5 s+2 J intercept. Then SMD=6 J/4.5 J=1.33. A safety margin of 1.33 is well below the margin of 3 achieved in the preferred embodiment.

Moreover, there is an important advantage of the preferred embodiment over prior art devices regarding the occasional need to deliver a second shock promptly to a patient. In the preferred embodiment, a second 18 J shock can be delivered within 4 seconds after the first, so that even in the worst case in which the elapsed time has reached the full DFT value, a 1.8 safety margin ratio is provided. Studies of sudden death in ICD patients show that repeated shocks with long times in fibrillation lead to electromechanical disassociation (EMD) death—even if the VF is finally converted. Thus, a device capable of rapidly delivering shocks (18 J every 4 seconds) is believed to have a better chance of saving the patient than a conventional device 34 J shock delivered every 12 seconds. These exemplary numbers can scale to more rapid shocks in both cases with different component technologies.

The preferred embodiment has a 8.2 to 8.5 ml battery that can achieve 4.5 amperes. It appears feasible with 125 to 135 $cm^2$ of cathode surface area to operate at 33 to 36 $mA/cm^2$). This would be a Lithium Silver Vanadium Oxide battery manufactured at Wilson Greatbatch Technologies in Clarence, N.Y. The capacitor is preferably a single HV cap, from CM Components Inc. (Williamsville, N.Y.) technology.

The capacitor would store 14 J at 750V to 775V with a capacitance of about 47 to 50 $\mu F$, and a volume of 4.5 ml. In alternative embodiments that expand these ranges without departing from the principles and advantages discussed herein, the capacitor has a capacitance of less than 60 $\mu F$., and the battery and circuitry operate to charge the capacitor to at least 700 volts. The transformer will be larger than that in conventional designs (1.2 ml vs. 0.6 ml).

While described in terms of a preferred embodiment, the invention need not be so limited. For instance, the numerical values are anticipated to change as technology advances. While the volume ratios discussed above are indicative of current technologies, and the ratios may remain approximately the same if volume efficiency of components advances at similar rates. However, if one of the battery or capacitor technologies advances by a large amount beyond the other, then the ratios discussed herein may shift. Nonetheless, the principles of the invention may be applied to the new technology using different ratios without departing from the fundamental concepts.

What is claimed is:

1. An implantable cardiac rhythm management device, comprising:
    a housing containing rhythm management circuitry;
    the circuitry including a battery, a transformer, and a single capacitor connected via charging circuitry operable to transmit current from the battery to charge the single capacitor;
    a plurality of electrodes connected to the circuitry and operable to transmit a shock from the single capacitor to cardiac tissue outside of the housing; and
    the combined volume of the battery and transformer being at least 1.5 times the volume of the single capacitor.

2. The device of claim 1 wherein the devices contains only a single battery.

3. The device of claim 1 wherein the capacitor has a capacitance of less than 50 $\mu F$.

4. The device of claim 1 wherein the battery charging power is greater than 4 watts.

5. The device of claim 1 wherein the capacitor has a volume less than 5 ml.

6. The device of claim 1 wherein the battery and capacitor are sized such that the battery is operable to charge the capacitor to at least 700 volts within 2 seconds.

7. The device of claim 1 wherein the battery and capacitor are sized based on a function of DFT levels with respect to time interval to deliver therapy.

8. The device of claim 1 wherein the battery and capacitor are sized to provide a safety margin ratio of delivered energy to DFT in the range of a local maximum at less than a selected charge time interval.

9. An implantable cardiac rhythm management device, comprising:
- a housing containing rhythm management circuitry;
- the circuitry including a battery, a transformer, and a single capacitor connected via charging circuitry operable to transmit current from the battery to charge the single capacitor;
- a plurality of electrodes connected to the circuitry and operable to transmit a shock from the single capacitor to cardiac tissue outside of the housing;
- the single capacitor having a capacitance of less than 50 $\mu$F; and
- the charge circuitry operable to charge the single capacitor to a voltage of at least 700 volts.

10. The device of claim 9 wherein the combined volume of the battery and transformer is at least 1.5 times the volume of the capacitor.

11. The device of claim 9 wherein the combined volume of the battery and transformer is between 1.5 and 2.5 times the volume of the capacitor.

12. The device of claim 9 wherein the battery is greater than 4 watts.

13. The device of claim 9 wherein the capacitor has a volume less than 5 ml.

14. The device of claim 9 wherein the battery and capacitor are sized such that the battery is operable to charge the capacitor to at least 700 volts within 2 seconds.

15. The device of claim 9 wherein the battery and capacitor are sized based on a function of DFT levels with respect to time interval to deliver therapy.

16. The device of claim 9 wherein the battery and capacitor are sized to provide a safety margin ratio of energy to DFT in the range of a local maximum at less than a selected charge time interval.

17. A method of operating an implantable cardiac rhythm management device having detection circuitry, a battery and a transformer connected via charging circuitry, the method comprising:
- in response to an abnormality detected by the detection circuitry, generating current flow from the battery to a single capacitor to charge the single capacitor;
- generating the current flow during a charging interval having a limited selected duration based on a DFT time function; and
- discharging the single capacitor to deliver a therapeutic shock after the charging interval;
- wherein the combined volume of the battery and transformer being at least 1.5 times the volume of the single capacitor.

18. The method of claim 17 wherein the charging interval is less than 2 seconds.

19. The method of claim 17 wherein the DFT time function provides that DFT decreases with a decreasing time interval for times below a selected time threshold, and wherein the charging interval is less than the time threshold.

20. The method of claim 17 wherein generating the current flow includes charging the capacitor to at least 700 volts.

* * * * *